United States Patent
Swierkowski

[11] Patent Number: 6,165,417
[45] Date of Patent: Dec. 26, 2000

[54] INTEGRATED TITER PLATE-INJECTOR HEAD FOR MICRODROP ARRAY PREPARATION, STORAGE AND TRANSFER

[75] Inventor: Stefan P. Swierkowski, Livermore, Calif.

[73] Assignee: The Regents of the University of California, Oakland, Calif.

[21] Appl. No.: 09/178,779

[22] Filed: Oct. 26, 1998

[51] Int. Cl.[7] .................................................. B01L 3/02
[52] U.S. Cl. ........................ 422/100; 422/99; 422/103; 436/180; 73/863.31
[58] Field of Search ............................... 422/63, 99, 100, 422/101, 103; 73/864.01, 864.11, 863.32, 864.13, 864.16, 864.17, 863.31; 101/366; 604/207, 208

[56] References Cited

U.S. PATENT DOCUMENTS

| | | | |
|---|---|---|---|
| 3,982,438 | 9/1976 | Byrd | 73/425.4 |
| 4,158,035 | 6/1979 | Haase et al. | 422/100 |
| 4,444,062 | 4/1984 | Bennett et al. | 73/863.32 |
| 4,461,328 | 7/1984 | Kenney | 141/67 |
| 4,511,534 | 4/1985 | Bennett, Jr. et al. | 422/100 |
| 4,537,231 | 8/1985 | Hasskamp | 141/238 |
| 4,626,509 | 12/1986 | Lyman | 435/287 |
| 4,931,400 | 6/1990 | Jitsukawa | 435/287 |
| 5,746,975 | 5/1998 | Chateau | 422/61 |
| 5,763,278 | 6/1998 | Sickinger et al. | 436/180 |
| 5,772,967 | 6/1998 | Wannlund et al. | 422/102 |
| 5,800,778 | 9/1998 | Chen et al. | 422/48 |
| 5,853,894 | 12/1998 | Brown | 428/422 |

FOREIGN PATENT DOCUMENTS

WO97/15394  5/1997  WIPO.

Primary Examiner—Maureen M. Wallenhorst
Assistant Examiner—Dwayne K. Handy
Attorney, Agent, or Firm—Daryl S. Grzybicki; L. E. Carnahan; Alan H. Thompson

[57] ABSTRACT

An integrated titer plate-injector head for preparing and storing two-dimensional (2-D) arrays of microdrops and for ejecting part or all of the microdrops and inserting same precisely into 2-D arrays of deposition sites with micrometer precision. The titer plate-injector head includes integrated precision formed nozzles with appropriate hydrophobic surface features and evaporative constraints. A reusable pressure head with a pressure equalizing feature is added to the titer plate to perform simultaneous precision sample ejection. The titer plate-injector head may be utilized in various applications including capillary electrophoresis, chemical flow injection analysis, microsample array preparation, etc.

18 Claims, 2 Drawing Sheets

INTEGRATED TITER PLATE-INJECTOR HEAD FOR MICRODROP ARRAY PREPARATION, STORAGE AND TRANSFER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to titer plates, particularly to titer plates for microdrop sampling apparatus, and more particularly to an integrated titer plate-injector head for microdrop preparation, storage and transfer.

Current emerging gene sequencing technology, for example, requires the injection of many (e.g., 96–384) microdroplet samples in the range of 0.2 to 2.0 $\mu$ liters, into arrays of small wells in instrumentation, such as electrophoresis plates.

In order to efficiently and reproducibly introduce the samples, it is highly desirable to avoid hand pipetting procedures, and use a technology that is amenable to robotics. Current procedures require a large amount of sample preparation and processing that results in small liquid samples stored in plastic, disposable titer plates, inside small, simple one-sided wells. Samples must then be extracted from these storage plates with miniature pipettes and placed elsewhere for subsequent analysis or further sample processing.

There are several major problems with current technology that picks up samples with either pipettes or pin grids, including: (1) pipette usage is difficult to control the sample placement and volume with very high precision; (2) pins used to pick up samples have limitations on sample size: larger samples need larger pins and these won't fit into current apparatus for placement of the sample; (3) pick-up of samples generally require larger samples to be prepared, not all of which are used, and this is a major cost factor when expensive or rare samples are involved; (4) pick-up and placement consists of two accurate mechanical procedures; and (5) sample pick-up and placement requires extra steps to sterilize the transfer tool unless it can be made disposable.

The present invention overcomes or simplifies the problems set forth above by eliminating pipette or pin usage, eliminates waste of sample material, eliminates the pick-up procedure for samples, and makes the placement procedure simpler by using self-alignment features, and provides a disposable titer plate-injector. The above referenced problems are solved or reduced by the integrated titer plate-injector head of the present invention that not only can be used for sample preparation and storage, but adds the feature of miniature nozzles to each sample well, thus enabling sample transfer without pipette or pin grid pickup and mechanical transfer procedures that currently must be used. The titer plate-injector head of the present invention may be fabricated from cheap, disposable material by injection molding, for example.

SUMMARY OF THE INVENTION

It is an object of the present invention to overcome problems of the current microdrop sampling technology.

A further object of the invention is to provide an improved titer plate for microdrop sampling and sample preparation.

A further object of the invention is to provide an inexpensive disposable titer plate-injector head.

Another object of the invention is to provide an integrated titer plate-injector head for microdrop array preparation, storage and transfer.

Another object of the invention is to provide an improved titer plate for storing 2-D arrays of microdrops and which can be used with an injector head for ejecting the microdrops and injecting part, or all, precisely into 2-D arrays of deposition sites with micrometer precision.

Another object of the invention is to provide a titer plate-injector head which includes integrated precision formed nozzles with appropriate hydrophobic surface features and evaporative constraints.

Another object of the invention is to provide an integrated titer plate-injector head with a pressure equalizing feature to perform simultaneous precision sample injection.

Other objects and advantages will become apparent from the following description and accompanying drawing. The invention involves an integrated titer plate-injector head for microdrops which overcomes or reduces the problems of the current microdrop sampling technology. The invention provides for integrated storage and transfer of microdrops without pipette or pin grid pick-up and mechanical transfer procedures currently utilized. The integrated titer plate-injector head can be fabricated, such as by injection molding, from an inexpensive disposable material, such as plastic, and has 1-D or 2-D arrays of storage wells for samples and has integrated precision formed nozzles for precise microdrop formation and injection into the desired apparatus, such as a microchannel array plate, or another titer plate. The nozzles are provided with appropriate hydrophobic surface features and evaporative constraints. A reusable pressure head with a pressure equalizing feature is added to the titer plate-injector head to perform simultaneous precision sample ejection.

BRIEF DESCRIPTION OF THE DRAWINGS

The accompanying drawing, which is incorporated into and forms a part of the disclosure, illustrates an embodiment of the invention and, together with the description, serves to explain the principles of the invention.

DETAILED DESCRIPTION OF THE INVENTION

The present invention is directed to an integrated titer plate-injection head for preparation, storage and transfer (injection) of microdrop samples into a desired apparatus, such as a microchannel array plate of, for example, an electrophoresis analysis system. A key feature of the present invention is that it can be fabricated (e.g., injection molded) from inexpensive disposable material, such as plastic, and has 1-D or 2-D arrays of storage wells for the sample and nozzles at the bottom of the titer plate for very precise microdrop formation and ejection. The nozzles eject microdrops out into an air gap where they are subsequently injected into another titer plate or into microchannel array input wells. The invention utilizes self-aligning and spacing pins which are located in alignment holes in an associated apparatus to provide precision alignment. The titer plate-injection head, after sample filling, can be covered with commercially available, very thin cling-wrap plastic layers on the top and the bottom, to prevent evaporation, contamination, and nozzle clogging; and the layer of cling-wrap plastic on the bottom can be peeled off before ejection, and the layer on top may be left in place to isolate the drive mechanism used for ejecting the microdrop from the titer plate through the nozzles. The plastic wrap can be omitted where the titer plate-injector head is stored in high humidity.

Figure 1:
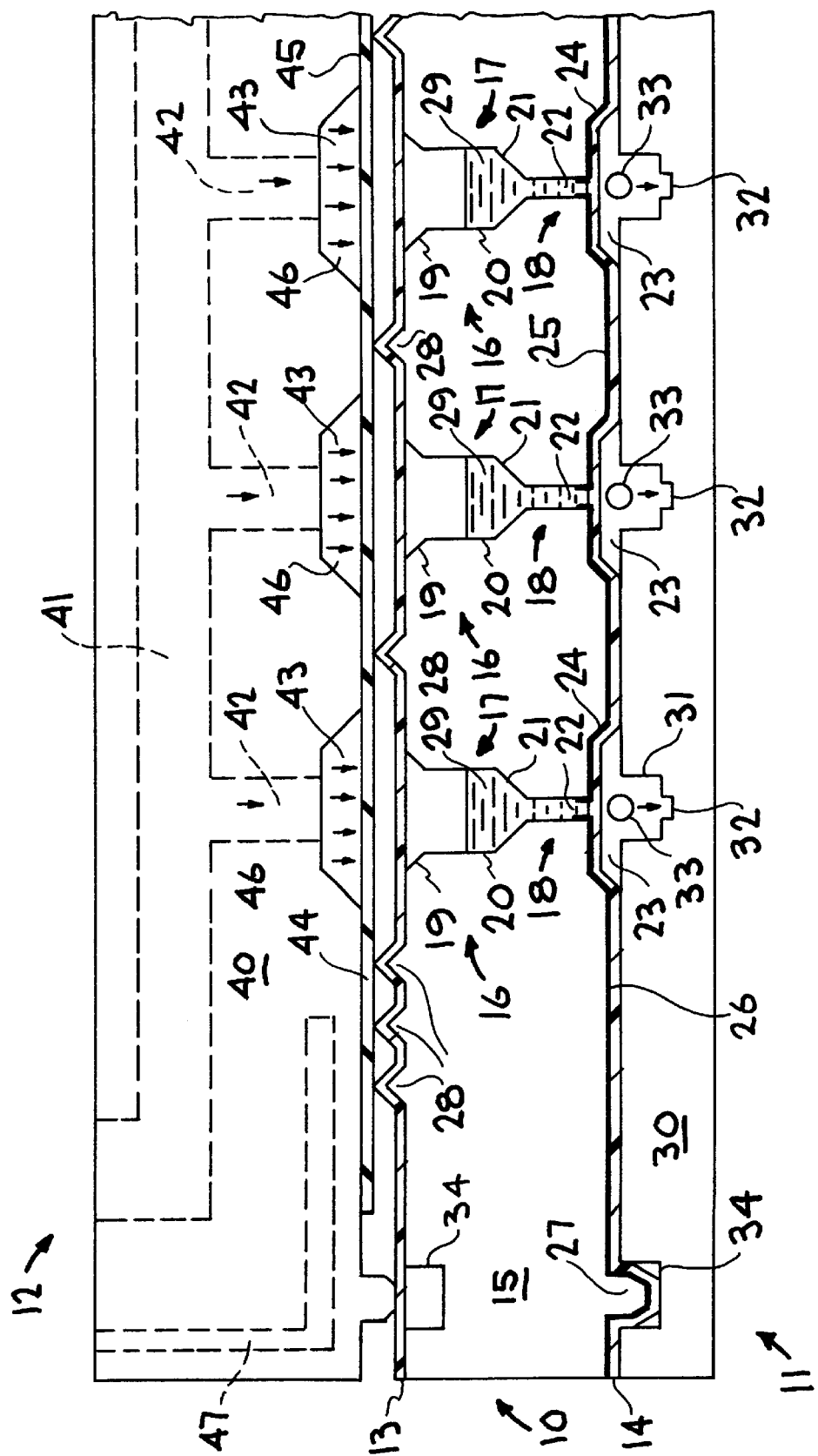
FIG. 1 is a partial cross-sectional view of an embodiment of the titer plate-injector head of the present invention positioned intermediate a microchannel array plate and a drive head assembly.

As shown in FIG. 1, the sample analysis assembly or apparatus is composed of the titer plate-injector head located intermediate a micro-channel array plate and a drive head. FIG. 1 shows small gaps, for clarity, between the three major components which gaps would be eliminated when the assembly is compressed before injection. Also, the thin cling-wrap plastic layer on the bottom of the titer plate-injector head, as shown, would be removed prior to ejection. The titer plate-injector head would be picked up (mechanically or by vacuum) by the reusable drivehead, and placed on the microchannel array plate, whereafter, as described in greater detail hereinafter, the drive head will supply one or more fluid (liquid or gas) pulses to a common drive membrane of the drive head to eject the microdrops of sample from the titer plate; the sample transfer volume can be metered. The drive head can, as shown in dash lines, have another manifold around the edges to serve as a vacuum pick-up for the titer plate. Also, the drive head need not register extremely precisely to the titer plate when picking it up, because the combination of major components is designed to self-align and self-level, as described hereinafter.

Key features of the titer plate-injector head include:

1. A hydrophobic coating, if necessary, on the bottom to prevent sample drainage and lateral wicking and enhance uniform droplet formation; the coating may extend partially into the nozzle exit.

2. A narrow nozzle that can support the sample by surface tension (e.g., ~50–300 $\mu$m).

3. Has built-in knife edge seals on the titer plate to seal each sample off and seal firmly against the complaint drive head membrane.

4. Below and opposite the top seal is a post (inverted pedestal) contacting the microchannel array plate, to supply pressure to the seal at the top.

5. Can be wrapped with cling-wrap plastic as described above to prevent evaporation, contamination, and nozzle clogging; and in high humidity storage conditions the cling-wrap plastic can be omitted.

6. Includes tapered alignment pins which cooperate with openings in the microchannel array plate for self-alignment and self-leveling, plus includes matching alignment holes for (a) titer plate stacking, and (b) ease of alignment to the drive head.

7. Includes rounded sample well corners at the top to stress relieve the drive head membranes.

8. The sample cup shape, above the nozzle, can be shaped to optimize the control over the volume and precision of the microdrop.

9. Has integrated precision formed miniature nozzles for each sample well.

10. Can perform simultaneous or single precision sample ejection.

11. The microchannel array plate could be replaced by another titer plate-injector head, for sample preparation.

12. A plurality of titer plate-injector heads may be utilized for the preparation of samples involving multiple components.

Referring now to the drawing, FIG. 1 illustrates an analysis system or assembly composed of three major components, with the integrated sample titer plate-injector head, indicated generally as 10 being located intermediate a microchannel array plate of an analytical instrument, indicated generally at 11, and a drive head, indicated generally at 12. The titer plate-injector head 10, as shown, includes top and bottom layers 13 and 14 of thin cling-wrap plastic for illustration purposes, but at the assembly stage, as shown for normal operation, the bottom layer 14 would have been previously peeled off.

The sample titer plate-injector head (TP-IH) 10 comprises a body member 15 composed of disposable plastic, for example, but may be constructed of other materials, such as silicon, glass, etc. Member 15 is provided with an array of openings extending therethrough, generally indicated at 16, only three being shown, each of which includes a sample well section 17 and a nozzle section 18. Each of the well sections 17 include an outer tapered wall 19 and straight wall 20, and an inner tapered wall 21, which opens into a reduced diameter opening 22 of nozzle section 18, which includes an enlarged opening or cutaway 23 having an outer tapered wall 24. Note that the top cling-wrap plastic layer 13 extends across the upper ends of openings 16 of well sections 17, and the bottom layer 14, prior to removal would extend across the lower end of opening 22 of nozzle section 18. Body member 15 includes lower flat surfaces 25, which form support posts or pedestals and are in contact with microchannel array plate 11 via a hydrophobic coating 26, which may be composed of fluorinated hydrocarbon, paralene, or polyimide, with a thickness of 100 nm to 5 $\mu$m. Note that the coating 26 extends into the openings 22 of nozzle section 18. Body member 15 and drive head 12 include a plurality of alignment pins or projections 27 with tapered outer ends located along lower edges of member 15 (only one shown each), and includes along the top surface thereof a plurality of knife edge seals 28 formed integral with the body member 15 and positioned around of each of well sections 17 of openings 16, which contain a sample 29.

By way of example, the body member 15 may have a length of 10 mm to 200 mm, width of 10 mm to 200 mm, thickness or depth of 1 mm to 10 mm; with the outer tapered walls 19 having a taper of 30° to 60° with an outer diameter of 1 mm to 7 mm and depth of 0.1 mm to 1 mm; with the straight walls 20 having a diameter of 1 mm to 7 mm and depth of 0.1 mm to 9 mm; with inner tapered walls having a taper of 30° to 60° and depth of 0.1 mm to 1 mm; with nozzle opening 22 having a diameter of 0.05 mm to 0.4 mm and length of 0.2 mm to 1 mm; with the openings or cutaways 23 having an inner diameter of 2 mm to 7 mm, an outer diameter of 3 mm to 8 mm, and a depth of 0.5 mm to 1 mm, with tapered walls 24 being at a taper of 30° to 60°; the knife edge seals 28 projecting a distance of 0.2 mm to 0.6 mm from the top surface of body member 15; and the alignment pins or projections 27 having a width of 1 mm to 2 mm, length of 1 mm to 10 nm.

Microchannel array plate 11 may, for example, be a component of an electrophoresis analysis assembly or system, and includes a body member 30 having an array of input wells 31, only three shown, each having in communication therewith a microchannel 32. Note that each input well 31 is located to be in alignment with the openings 16 of the TP-IH 10 such that nozzle sections 18 inject microdroplets 33 into the input wells 31 and thus into microchannels 32, as indicated by the arrows. TP-IH 10 and plate 11 each include a plurality of holes 34 (only one shown each) which are aligned with and adapted to receive the alignment pins or projections 27 for alignment of component 10 with component 11. The input wells 31 and alignment holes 34 may have a diameter of about 1 mm to 2 mm and a depth of about 1 mm to 10 mm. Microchannel array plates are known in the art and further description thereof is deemed unnecessary to understand its use with the present invention.

Drive head 12 comprises a body member 40 having a pneumatic drive manifold 41 with an array of manifold sections 42 (only three shown) connected to cutaways 43 in body member 40. A flexible drive membrane 44 is secured to the lower surface 45 of body member 40 and forms with cutaways 43 fluid chambers 46. Optionally, a vacuum manifold 47 schematically illustrated by dash lines may be formed in body member 40 of drive head 12 to enable pick-up of the TP-IH 10, as described above. In operation and with the drive head 12 positioned against TP-IH 10, the drive membrane 44 is in sealing contact with knife edge seals 28, and upon pneumatic pressure being directed through manifold 41 and manifold sections 42, as indicated by the arrows, the membrane 44 is expanded downwardly applying a compression force, due to air in sample wells 17, on sample 29 causing a microdrop 33 to pass (ejected) through nozzle section 18 and injected into input well 31 of microchannel array plate 11. While not shown, the manifold sections 42 may be individually controlled such that pneumatic pressure can be directed through one or all of sample well sections 17, whereby microdrops 33 can be ejected from one or all of nozzle sections 18.

Figure 2:
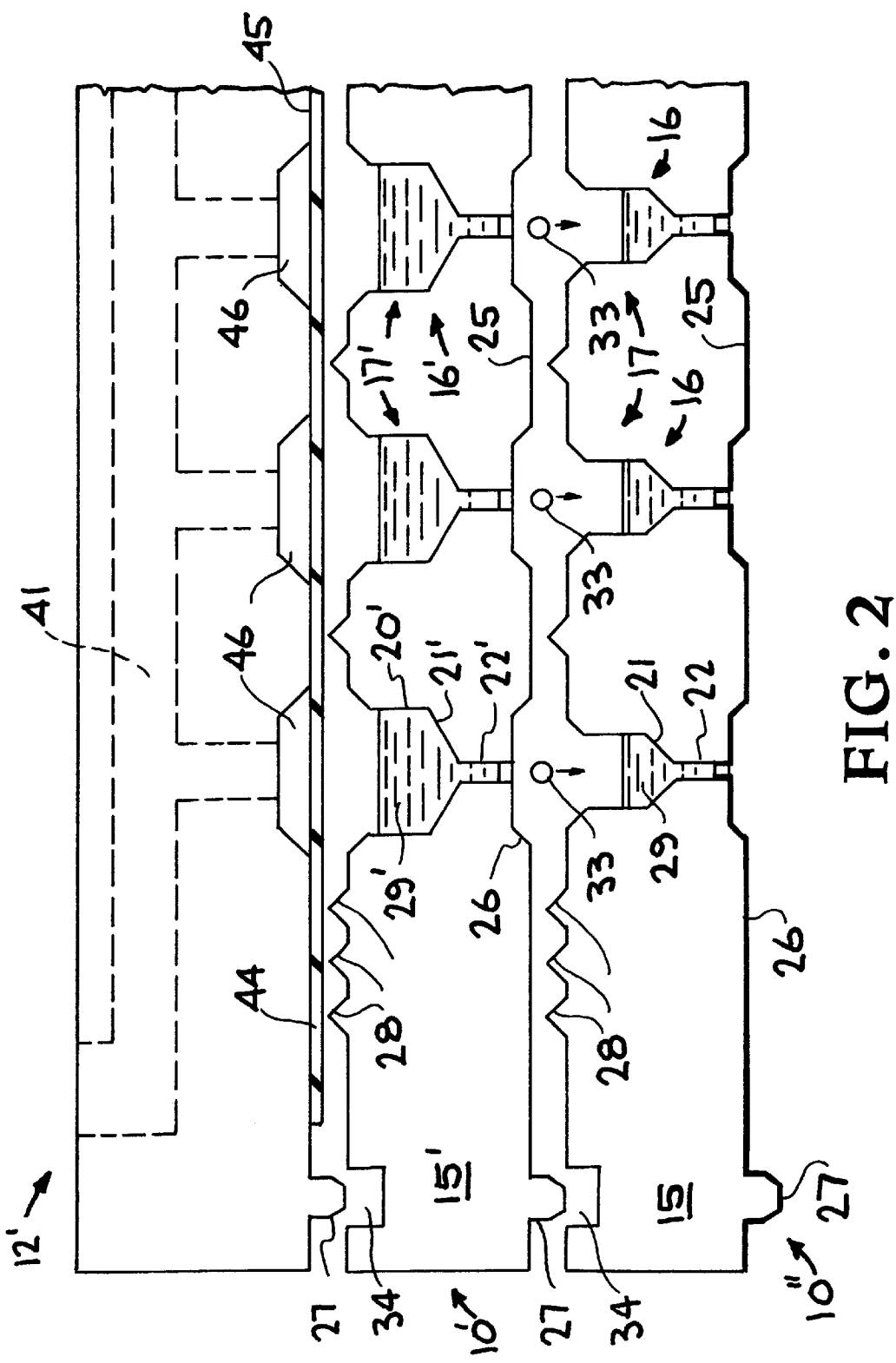
FIG. 2 illustrates in partial cross-sectional view an embodiment of an arrangement for preparation of samples and dispensing regents into a second titer plate.

FIG. 2 illustrates an embodiment of the invention utilizing a plurality of titer plates (only two shown), one being a sample preparation titer plate and the other a reagent titer plate-injector for the preparation of samples and dispensing of reagents. However, additional similar titer plates may be utilized. Each titer plate, generally indicated at 10' and 10" are similar in construction to the titer plate-injector head 10 of FIG. 1 and corresponding reference numbers. The drive head 12' is the same as drive head 12 of FIG. 1 and can be utilized to position either of titer plates 10' or 10" as described above with respect to FIG. 1. The only difference between the reagent titer plate-injector 10' and the sample titer plate 10" is the size of the sample well sections 17' of the openings 16' through the body member 15' of reagent titer plate-injector 10' are larger than the well sections 17 of openings 16 of sample preparation titer plate 10" for supply reagent 29'. Each of titer plates 10' and 10" is provided with a plurality of protruding members 27 and alignment holes 34, as described with respect to FIG. 1. By use of the two (or more) titer plate arrangements of FIG. 2, the titer plate-injector head of the present invention may be used to store various types of agents or material for preparation of samples to be injected into a microchannel array plate, such as plate 11 of FIG. 1 of an analytical instrument, such as an electrophoresis analysis system. The protective removable films 13 and 14 of FIG. 1 can be applied to the plates 10' and 10".

It has thus been shown that the present invention provides a solution to prior problems of sample preparation, sample storage, and microdrop transfer systems by providing an integrated titer plate-injector head for microdrop array preparation, storage, and transport. When combined with a cooperating microchannel array plate and drive head, the integrated titer plate-injector head enables precision alignment and sample transfer volume control, in addition to prevention of sample evaporation or contamination and nozzle clogging while the sample material is in storage therein. In addition, the titer plate-injector head can be fabricated, as by injection molding, from inexpensive disposable materials, and has 1-D or 2-D arrays of storage wells connected directly to precision nozzles for very precise microdrop formation and injection into a desired apparatus. The integrated titer plate-injector head can be utilized in numerous sampling applications, including capillary electrophoresis, chemical flow injection analysis, liquid chromatography, enhanced electrokinetic injection, chemical reaction microcapillary flow systems, combinational wet chemistry processing and analysis, and microsample array preparations.

While specific embodiments, materials, parameters, etc., have been described and/or illustrated, such are not intended to be limiting. Modifications and changes may become apparent to those skilled in the art, and it is intended that the invention be limited only by the scope of the appended claims.

The invention claimed is:

1. An integrated titer plate-injector head for microdrop array storage and transfer, comprising:
    a body member,
    said body member having openings extending therethrough,
    each of said openings being constructed to define a sample well section at one end and a nozzle section at an opposite end,
    each said nozzle section including a cutaway section in a flat surface of said body member forming an outer end of said opening, and
    seal means located adjacent said sample well section of each opening.

2. The apparatus of claim 1, wherein said body member additionally includes a plurality projecting members to provide alignment with associated devices.

3. The apparatus of claim 1, wherein said body member additionally includes a flat bottom surface adjacent said nozzle sections of said openings.

4. The apparatus of claim 1, wherein said sample well section of each of said openings includes a rounded top section to stress relieve an associated drive membrane.

5. The apparatus of claim 1, additionally including a layer of cling-wrap material on at least the top and bottom surfaces of said body member.

6. The apparatus of claim 1, additionally including a hydrophobic coating on a bottom surface of said body member.

7. The apparatus of claim 6, wherein said hydrophobic coating extends up to or into said nozzle sections of said openings.

8. The apparatus of claim 1, wherein said seal means comprise knife edge seals located on an upper surface of said body member.

9. The apparatus of claim 1, wherein said seal means are integral with said body member.

10. The apparatus of claim 1, wherein said body member additionally includes a plurality of openings in an upper surface to enable alignment with another body member.

11. The apparatus of claim 1, wherein said sample well sections include an outer tapered wall section, a straight wall section, and an inner tapered wall section; and wherein said nozzle section includes a straight wall section and said cutaway section, said straight wall section of said nozzle section being connected to said inner tapered wall section said sample well section and of a diameter less than a diameter of said straight wall section of said sample well section, and said cutaway section being connected to said straight wall section of said nozzle section and having a tapered wall section.

12. The apparatus of claim 1, in combination with a microchannel array plate and a drive head, said microchannel array plate having an array input well located to align with said nozzle sections of said titer plate-injector head for receiving microdrops ejected from said nozzle section; and said drive head including a flexible drive membrane located in alignment with said sample well sections of said titer plate-injector head for ejecting sample material from said sample well sections.

13. In a sampling system, the improvement comprising:
an integrated titer plate-injector head having an array of interconnected sample containing wells and microdroplet ejection nozzles, said microdroplet ejection nozzles each including an outer cutaway section, and
removable means for preventing sample evaporation and contamination, and preventing nozzle clogging.

14. The improvement of claim 13, additionally including a coating of hydrophobic material adjacent the ejection nozzles.

15. The improvement of claim 13, additionally including means for enabling self-alignment of the titer plate-injector with an associated component of a sampling system, analytical system, or storage system.

16. The improvement of claim 13, additionally including sealing means formed integral with said titer plate-injector head.

17. The sampling system of claim 12, including said titer plate-injector head located intermediate a microchannel array plate and a drive head, said drive head having been constructed to eject sample material from said sample containing wells through said ejection nozzles to form microdroplets injected into input wells in said microchannel array plate.

18. The sampling system of claim 17, wherein said titer plate-injector head and said microchannel array plate includes means for aligning same to assure that said input wells and said ejection nozzles are aligned.

* * * * *